United States Patent
Takagi et al.

(10) Patent No.: US 6,498,028 B1
(45) Date of Patent: Dec. 24, 2002

(54) METHOD FOR ENRICHING AND ISOLATING BACTERIA WHICH AEROBICALLY DEGRADES PCNB

(75) Inventors: Kazuhiro Takagi, Ibaraki (JP); Yuuichi Yoshioka, Kochi (JP)

(73) Assignee: National Institute for Agro-Environmental Science Independent Administrative Institute, Tsukuba (JP)

(*) Notice: Subject to any disclaimer, the term of this patent is extended or adjusted under 35 U.S.C. 154(b) by 0 days.

(21) Appl. No.: 09/462,877

(22) PCT Filed: May 11, 1999

(86) PCT No.: PCT/JP99/02420

§ 371 (c)(1),
(2), (4) Date: Mar. 24, 2000

(87) PCT Pub. No.: WO99/60098

PCT Pub. Date: Nov. 25, 1999

(30) Foreign Application Priority Data

May 18, 1998 (JP) ............................................. 10-135156

(51) Int. Cl.[7] .......................... C12N 1/20; C07G 17/00; C12M 1/00; C12M 3/00
(52) U.S. Cl. ................. 435/253.3; 435/262; 435/253.6; 435/267; 435/290.1; 435/289.1
(58) Field of Search .............................. 435/290.1, 262, 435/262.5, 253.3, 253.6, 267, 289.1

(56) References Cited

U.S. PATENT DOCUMENTS

| | | | |
|---|---|---|---|
| 4,493,895 A | * | 1/1985 | Colaruotolo et al. ....... 435/262 |
| 4,859,594 A | * | 8/1989 | Portier .................... 435/172.1 |
| 5,998,198 A | * | 12/1999 | Nakayama et al. ...... 435/262.5 |

FOREIGN PATENT DOCUMENTS

| | | |
|---|---|---|
| JP | 09075074 | 3/1997 |
| JP | 09085283 | 3/1997 |
| JP | 10225288 | 8/1998 |

* cited by examiner

Primary Examiner—Jon P. Weber
Assistant Examiner—Patricia Patten
(74) Attorney, Agent, or Firm—Rader, Fishman & Grauer PLLC (57) ABSTRACT

It is an object of the invention to improve a conventional soil percolation technique to thereby provide a method of enriching and isolating decomposing bacteria decomposing an organochlorine agricultural chemical PCNB which is difficult to decompose, in a short time period, and to provide decomposing bacteria for efficiently processing PCNB. To practice the method, an enrichment soil layer 2 is formed by mixing a soil containing an organochlorine agricultural chemical PCNB with a fragmented porous material having an infinite number of micropores and at the same time a greater adsorptivity for adsorbing PCNB than the soil, and an inorganic salt medium 3 containing a carbon and nitrogen source, the carbon and nitrogen source being formed by only PCNB, is circulated through the enrichment soil layer 2, thereby enriching the aerobic bacteria *Burkholderia cepacia* in the fragmented porous material.

16 Claims, 9 Drawing Sheets

| MICROHABITAT | pH (H2O) | BET-SINGLE POINT DETERMINATION SPECIFIC AREA (m2/g) | PERCENTAGE OF CUMULATIVE MICROPORE VOLUMES CALCULATED FOR RESPECTIVE RANGES OF DIAMETERS OF MICROPORES (%) | | | | | | | |
|---|---|---|---|---|---|---|---|---|---|---|
| | | | DIAMETER OF MICROPORES (μm) | | | | | | | |
| | | | 200~100 | 100~50 | 50~20 | 20~10 | 10~5 | 5~1 | 1~0.003 | |
| A | 7.8 | 99.9 | 3.0 | 6.5 | 9.8 | 6.4 | 5.8 | 16.5 | 52.3 | |
| B | 5.5 | 72.1 | 5.4 | 4.3 | 9.0 | 6.6 | 5.4 | 9.3 | 60.1 | |
| C | 10.4 | 208.6 | 0.2 | 2.3 | 15.8 | 15.0 | 1.0 | 12.9 | 52.6 | |
| D | 8.1 | 555.7 | 0.0 | 2.5 | 20.0 | 25.4 | 7.5 | 22.5 | 22.1 | |
| E | 9.6 | 1020.9 | 0.8 | 0.9 | 1.4 | 1.8 | 3.2 | 29.0 | 63.2 | |

| | | PD1 | PD3 | PD6 |
|---|---|---|---|---|
| GRAM STAINING | | NEGATIVE | NEGATIVE | NEGATIVE |
| SHAPE | | SINGLE ROD BACTERIA | SINGLE ROD BACTERIA | SINGLE ROD BACTERIA |
| MOTILITY | | NONE | NONE | NONE |
| COLOR OF COLONY | | YELLOW | YELLOW | YELLOW |
| ALIPHATIC ACID OF BODIES OF BACTERIA | ALIPHATIC ACID CONTENT (%) | 14:0 | 4.3 | 2.9 | 3.5 |
| | | 3-OH-14:0 | 16.8 | 19 | 15 |
| | | i-16:0 | 11 | 12.8 | 15 |
| | | 16:0 | 14.4 | 17.4 | 16.5 |
| | | 3-OH-16:0 | 24.7 | 19.3 | 16.8 |
| QUINONE CONTENT (%) | | 99.2 | 96.9 | 95.9 |
| CONTENT OF G+C (mol%) | | 65.8 | 65.6 | 65.8 |

METHOD FOR ENRICHING AND ISOLATING BACTERIA WHICH AEROBICALLY DEGRADES PCNB

RELATED APPLICATIONS

This application is a national stage application under 35 USC 371 and claims priority from PCT/JP99/02420, filed May 11, 1999, which claims priority from Japanese Patent Application No. 135156/1998, filed May 18, 1998. This application is also related to Japanese Patent Application No. Hei 9-30176. All of these applications are incorporated herein by reference.

TECHNICAL FIELD

This invention relates to a technique of enriching decomposing bacteria which can be used to treat soil polluted by organochlorine compounds, such as agricultural chemicals, particularly to prevent contamination of river water and groundwater caused by agricultural chemicals in soil, and a technique of isolating the decomposing bacteria by utilizing the enriching technique, and more particularly to techniques of these kinds for enriching and isolating decomposing bacteria for decomposing organochlorine agricultural chemicals difficult to decompose.

BACKGROUND ART

To maintain today's agricultural production, agricultural chemicals cannot be dispensed with, and to conserve flora in golf courses or the like as well, agricultural chemicals are used in large quantities. On the other hand, there is a concern that agricultural chemicals work as contaminants to have undesirable effects on the environment, especially to be a pollution source of river water and groundwater. An organochlorine agricultural chemical pentachloronitrobenzene ("PCNB") used for killing bacteria causing soil disease is pointed out to be one of contaminants causing such a pollution. PCNB is an organochlorine compound very difficult to decompose, and as matters stand, a method of efficiently disposing PCNB remaining in soil and the like has not been proposed.

To restore soil contaminated by organochlorine compounds, such as agricultural chemicals, with decomposing bacteria has been considered to be a useful technique. This technique makes use of decomposing bacteria, among microbes inhabiting in soil in enormous numbers, which are capable of decomposing organic compounds serving as functional skeletons in agricultural chemicals and the like, thereby rendering the organic compounds harmless or eliminating the same from the environment. Therefore, it is possible to eliminate contaminants, such as agricultural chemicals or the like, from the environment by collecting bacteria which are capable of decomposing organochlorine compounds and exploiting such capabilities of the decomposing bacteria.

The method of selective enrichment/isolation of a specific kind of bacteria from various soil-inhabiting bacteria includes a soil percolation technique in which a column or the like is filled with soil containing inhabiting decomposing bacteria to form an enrichment soil layer, and an inorganic salt medium, which contains only organochlorine compounds, such as agricultural chemicals, as solo carbon and nitrogen sources, is continuously circulated through the enrichment soil layer, whereby a specific kind of decomposing bacteria, that is, decomposing bacteria which is capable of using the carbon or nitrogen source contained in the inorganic salt medium for assimilation or co-metabolism is selectively enriched for isolation. Actually, however, the above conventional soil percolation technique generally takes a long time period of one half to one year to enrich and isolate decomposing bacteria, and depending on the kind of an organic compound, there are cases where no suitable decomposing bacteria can be enriched by the method. The fact that such a long time period is required is a large impediment encountered in putting to practical use the river water or groundwater pollution control technique using decomposing bacteria.

The present invention has been made under these circumstances, and an object thereof is to improve the conventional soil percolation technique to thereby provide a method of enriching and isolating decomposing bacteria capable of decomposing an organochlorine agricultural chemical PCNB which is difficult to decompose, in a short time period, and to provide decomposing bacteria for efficiently disposing of PCNB.

DISCLOSURE OF THE INVENTION

To attain the object, the present inventors have improved the conventional soil percolation technique in the following respects, and thereby established the technique which is capable of largely enhancing the speeds of enrichment and isolation of decomposing bacteria. The gist of the improvement is that a porous material having an infinite number of micropores is fragmented to pieces of approximately several mm to ten and several mm in size such that the porous material can be handled with ease and at the same time has a large effective surface area, and then the fragmented porous material is mixed into an enrichment soil layer as an artificial microhabitat. According to this technique, decomposing bacteria can be effectively enriched and isolated over a time period of approximately three weeks to three months, although the required time period is slightly different depending on the kind of a contaminant and the kind of bacteria decomposing the contaminant. The inventors have already filed a patent application concerning the technique (Japanese Patent Application No. Hei 9-30176).

According to the present invention, by using the improved soil percolation technique, a specific kind of decomposing bacteria were selectively enriched and isolated by continuously circulating an inorganic salt medium containing an organochlorine agricultural chemical PCNB as only sources of carbon and nitrogen to the enrichment soil layer. As a result, aerobic bacteria could be obtained in a very short time period which effectively carries out complete decomposition of PCNB. Out of the enriched and isolated decomposing bacteria, three strains which have a high PCNB-decomposing activity were examined for identification, and it was found that the three strains belong to aerobic bacteria named *Burkholderia cepacia*. As far as the inventors know, decomposing bacteria for decomposing PCNB are mostly anaerobic bacteria, and *Burkholderia cepacia* obtained by the improved soil percolation technique (*Burkholderia cepacia* KTYY97, National Institute of Bioscience and Human Technology Agency of Industrial Science and Technology, 1–3, Higashi 1-chrome, Tsukuba-shi, Ibaraki 305-8566, Japan, Receipt No. FERM BP-6721, Received May 18, 1998, hereinafter referred to as "the present decomposing bacteria") provides possibility of quite novel uses since this bacteria are aerobic and completely decomposes or degrades PCNB.

It is found that if a loopful—using an inoculating needle—of the present decomposing bacteria is added to 30 ml of an inorganic salt medium containing PCNB in a concentration of 3 to 4 mg/liter, it is possible to completely decompose PCNB in approximately five days such that all chlorine atoms bonded to each PCNB molecule are removed from the molecule. Further, the study of the present inventors revealed that the present decomposing bacteria are capable of decomposing even an organochlorine agricultural chemical CNP which has been conventionally considered to be very difficult to decompose. Aerobic bacteria, such as the present decomposing bacteria, are less restricted in the manner of handling the same, unlike anaerobic bacteria, and hence only by applying the present decomposing bacteria to a soil contaminated by PCNB, it is possible to effectively decompose the PCNB, which makes it possible to prevent river water and groundwater pollution.

The present decomposing bacteria can be enriched and isolated by the improved soil percolation technique proposed by the present inventors. This method comprises mixing a soil containing an organochlorine agricultural chemical PCNB with a fragmented porous material having an infinite number of micropores and at the same time a greater adsorptivity for adsorbing PCNB than the soil to form an enrichment soil layer, and circulating through the enrichment soil layer an inorganic salt medium containing a carbon and nitrogen source, the carbon and nitrogen source being formed by only PCNB, thereby enriching the decomposing bacteria in the fragmented porous material.

The soil containing the organochlorine agricultural chemical PCNB is preferably a soil continuously using PCNB as an agricultural chemical. The present decomposing bacteria are hardly populated in ordinary soils, and on the other hand, is relatively thickly populated in a soil using PCNB. Therefore, by making use of such a soil, the present decomposing bacteria can be efficiently enriched.

It is preferred that the fragmented porous material used for the enrichment is formed by fragmenting a porous material having an infinite number of micropores, such as charcoal, to pieces of several to ten and several mm in size, and the fragmented porous material is mixed as an artificial microhabitat into the enrichment soil layer. Further, to carry out speedy enrichment of the present decomposing bacteria, it is preferable to use charcoal of broad-leaved tree which is baked at a low or medium temperature of approximately 400 to 700° C., with a volume ratio of micropores with a diameter of approximately 5 to 20 $\mu$m to a total of micropores being 10% or more, the inside of micropores being slightly alkaline with pH of approximately 7 to 8, and further with a specific surface area of the material being approximately 80 to 120 $m^2$/g. The results of experiments of enrichment made by using various artificial microhabitats different in micropore distribution, pH within micropores, and specific surface area showed that the artificial microhabitat satisfying the above conditions makes it possible to enrich the present decomposing bacteria at a highest speed and with a highest efficiency. Presumably, this is because the artificial microhabitat satisfying the above conditions is readily inhabited by the present decomposing bacteria and a manner of adsorption of PCNB in the micropores permits the present decomposing bacteria to use PCNB efficiently.

The method of isolating the present decomposing bacteria is carried out by using the above enriching method, and comprises mixing a fragmented porous material having the present decomposing bacteria enriched therein into a new fragmented porous material to form an enrichment layer consisting of the fragmented porous materials only, and circulating through the enrichment layer an inorganic salt medium containing a carbon and nitrogen source, the carbon source and the nitrogen source being formed by only PCNB, thereby effecting enrichment of the present decomposing bacteria in the new fragmented porous material as well to increase a degree of enrichment of the present decomposing bacteria, for isolation thereof. To carry out this isolating operation at a high speed and with efficiency, it is preferred that the artificial microhabitat satisfying the above conditions be used as the new fragmented porous material and the isolating operation be repeatedly carried out.

Further, the fragmented porous material having the present decomposing bacteria enriched therein by the enriching and isolating methods according to the invention can be used as an organochlorine agricultural chemical-decomposing bacteria holdback carrier. Thus, the capability of taking out the present decomposing bacteria in the form of a microhabitat which can be easily handled, i.e. as a carrier holding the present decomposing bacteria facilitates application of the holdback carrier holding the present decomposing bacteria to a soil contaminated by PCNB, e.g. mixing the same into a target soil where PCNB should be disposed of, and makes it possible to decompose PCNB in the soil without providing a special facility.

DESCRIPTION OF REFERENCE NUMERALS

1: soil layer tank;
2: enrichment soil layer (enrichment layer);
3: inorganic salt medium; and
4: solution storage tank

BEST MODE FOR CARRYING OUT THE INVENTION

Figure 1:
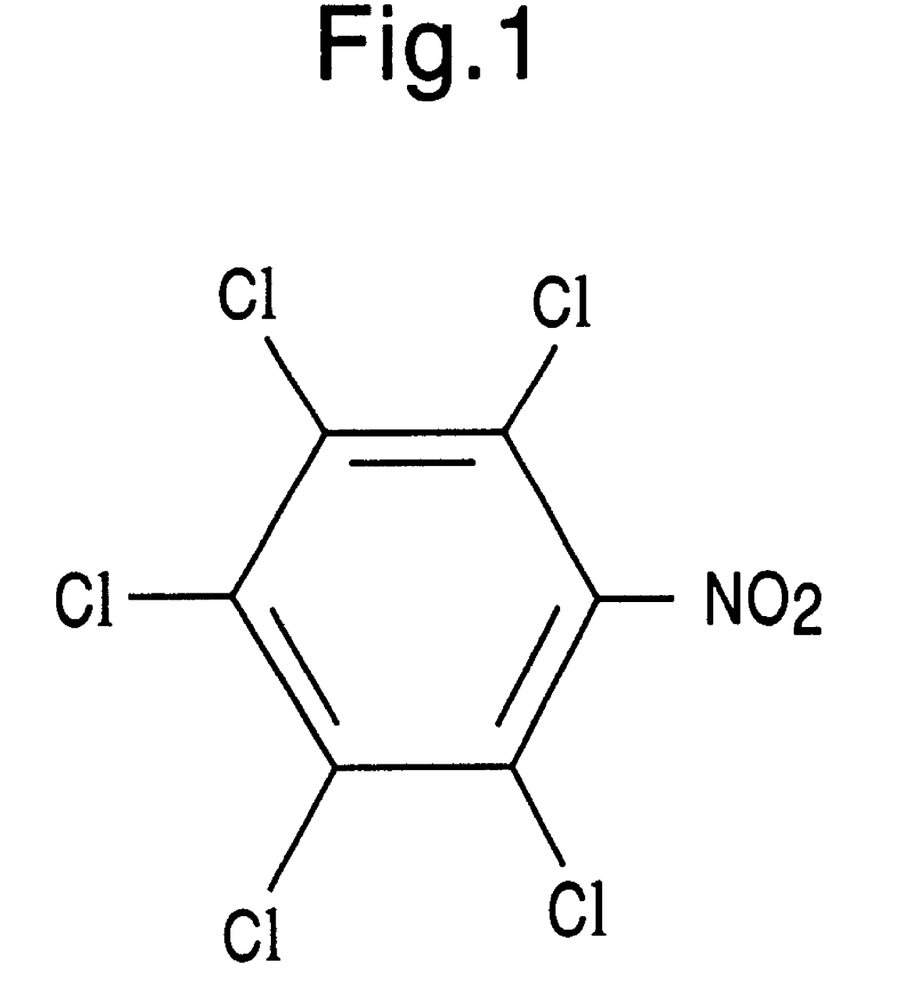
FIG. 1 is a diagram showing a structural formula of PCNB.
Figure 2:
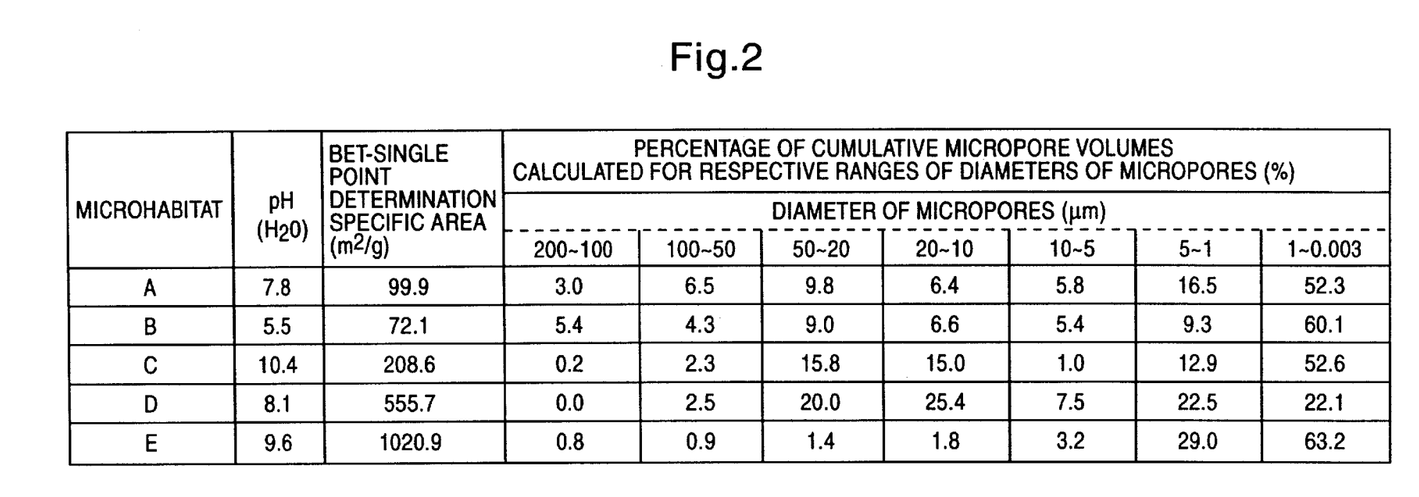
FIG. 2 shows a table showing physical properties of each artificial microhabitat used in the present embodiment.

The embodiment of the invention will now be described. The enrichment of decomposing bacteria decomposing PCNB by the improved soil percolation technique proposed by the present inventors was carried out under the following conditions:

agricultural chemical to be tested: standard product of PCNB (structural formula thereof is shown in FIG. 1);

soil to be tested: soil of a field repeatedly using PCNB, sieved to soil material having a size of 2 mm or less;

circulating solution: inorganic salt medium containing 10 mg/liter of PCNB as solo sources of carbon and nitrogen; and circulating conditions: 25° C., a dark place As artificial microhabitats for enrichment, out of artificial microhabitats A to E having respective physical properties listed in Table of FIG. 2, an artificial microhabitat A was employed. The following materials A to E in the table are defined as follows:

A: charcoal formed by normally baking a wood of broad-leaved tree at a normal baking temperature of 500° C. (this temperature shall apply for a normal baking temperature hereafter) and fragmenting to pieces of 5 to 10 mm;

B: chitosan-treated charcoal formed by normally baking a wood of broad-leaved tree and fragmenting to pieces of 5 to 10 mm;

C: charcoal formed by further baking charcoal formed by normally baking a wood of broad-leaved tree, at 1000° C. for 4 hours, and fragmenting to pieces of 5 to 10 mm;

D: charcoal formed by baking conifer wood at 1000° C. for 8 hours and fragmenting to pieces of 5 to 10 mm; and E: commercially available granular activated carbon (grain diameter of 5 mm).

Figure 3:
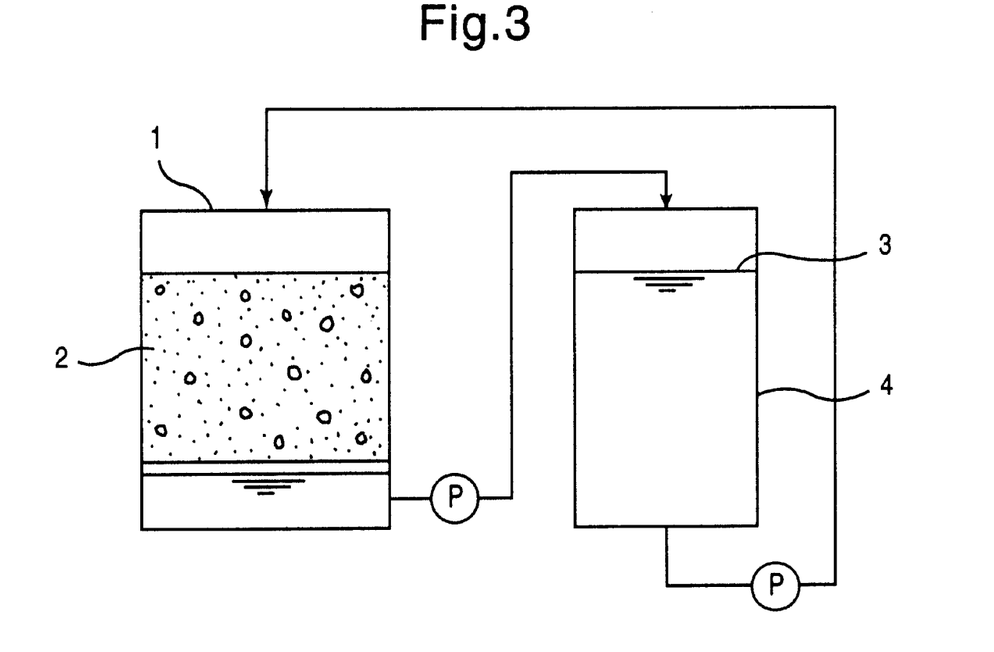
FIG. 3 is a diagram schematically showing a device used in an enriching and isolating methods of the embodiment.

The enrichment of decomposing bacteria according to the embodiment is carried out in the following manner: As shown in FIG. 3, an enrichment soil layer 2 was formed in a soil layer tank 1 having a volume of 500 ml. The enrichment soil layer 2 is formed by mixing 2 g of the artificial microhabitat A fragmented to pieces of approximately 5 to 10 mm into 40 g of a soil under test. An inorganic salt medium 3 (300 ml) containing PCNB as solo sources of carbon and nitrogen is caused to circulate from a solution storage tank 4 to the enrichment soil layer 2, for enrichment in a dark place at 25° C.

Figure 4:
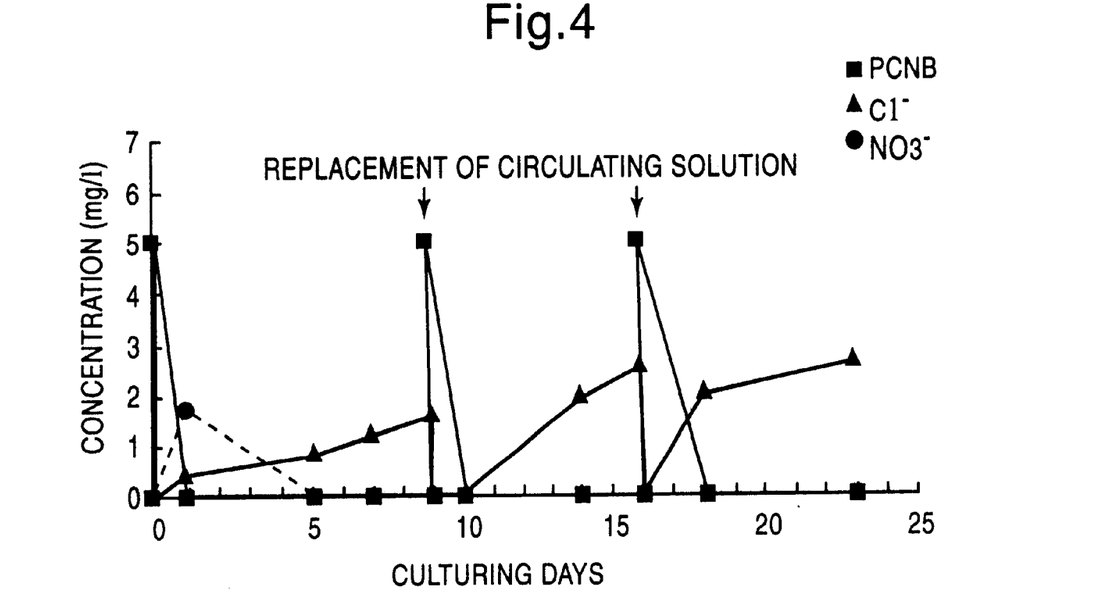
FIG. 4 shows a graph showing changes in concentrations of PCNB, $Cl^-$ (chloride) and $NO_3^-$ (nitrate) in a PCNB-containing circulating solution during an enriching operation of the present embodiment.

The results of measurement of concentrations of PCNB, as well as concentrations of $Cl^-$ (chloride) and $NO_3^-$ (nitrate) as by-products of decomposition of PCNB in the circulating solution during the enrichment operation are shown in FIG. 4. In FIG. 4, when attention is paid to the concentration of $Cl^-$, it is recognized that after a first replacement of circulating solutions (which means that at this time point a circulating solution in use is replaced by a new circulating solution newly prepared; the same applies in the following), the rate of increase in the concentration of $Cl^-$ tends to become higher, and it is confirmed that after a second replacement of circulating solutions, the rate of increase in the concentration of $Cl^-$ is drastically increased, meaning that the enrichment of the decomposing bacteria is in progress. The rate of increase in the concentration of $Cl^-$ becomes larger in a manner proportional to the progress of the enrichment of decomposing bacteria, and means that decomposition of PCNB is being more actively carried out accordingly.

Figure 5:
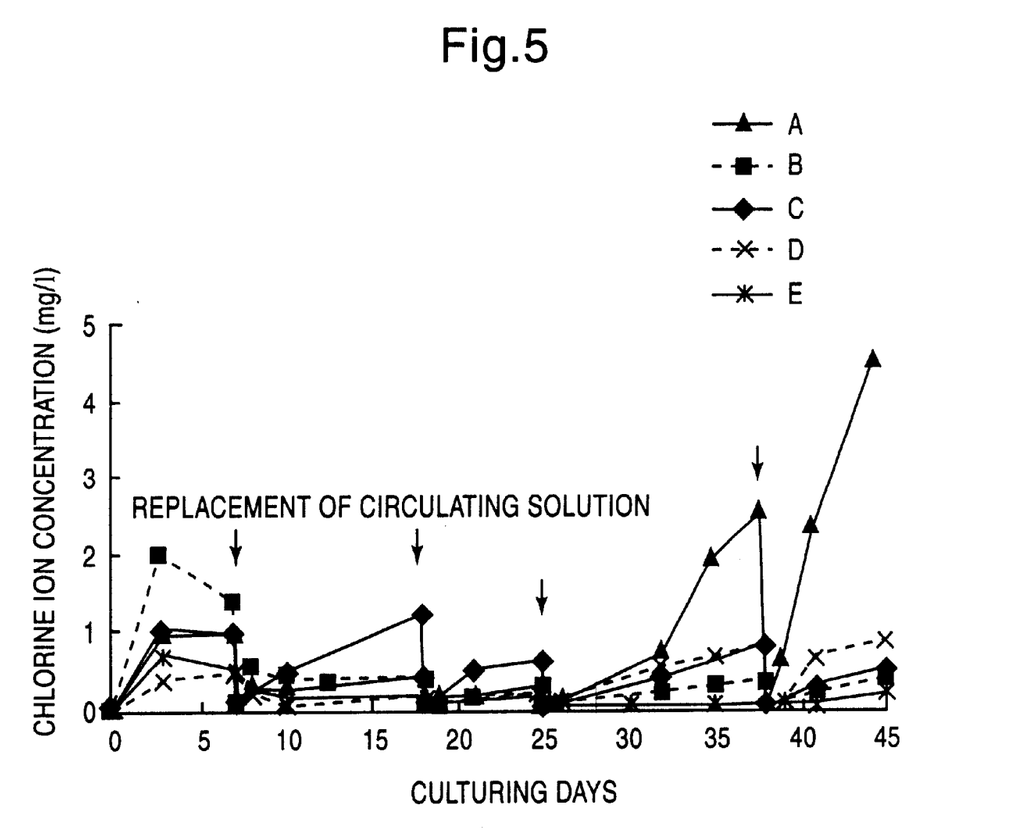
FIG. 5 shows a graph showing differences in enriching speeds of PCNB-decomposing bacteria in the respective artificial microhabitats during an isolating operation of the present embodiment, in relation to concentrations of chlorine ions ($Cl^-$)

Then, the artificial microhabitat A having the decomposing bacteria enriched therein by the above enriching operation was taken out, and 0.25 g of the artificial microhabitat A with enrichments and 7.5 g of each of new artificial microhabitats A to E are mixed to prepare six kinds of enrichment layers for isolating the PCNB-decomposing bacteria. The operation for isolating the decomposing bacteria according to the embodiment is carried out by forming the enrichment layers in place of the enrichment soil layer 2 shown in FIG. 3 in the soil layer tank 1, and circulating the inorganic salt medium 3 containing PCNB as solo sources of carbon and nitrogen through the enrichment layer under the same conditions as the enriching operation. The results of measurement of concentration of chlorine ions ($Cl^-$) as a by-product of decomposition of PCNB when the isolating operation is carried out using the six kinds of artificial microhabitats A to E are shown in FIG. 5. As can be understood from the graph of FIG. 5, it is confirmed that only in the case of the enrichment layer formed by using the artificial microhabitat A, the rate of increase in the concentration of $Cl^-$ after a third replacement of circulating solutions becomes higher, and after a fourth replacement of circulating solutions, the rate of the increase is steeply increased.

Next, the capability of the decomposing bacteria decomposing PCNB obtained by the enriching and isolating operations of the embodiment will be described. The enriching and isolating operations described above are carried out by using the artificial microhabitat A, and 1.0 g of the resulting artificial microhabitat A with enrichments is broken to pieces, and properly diluted by using a phosphate buffer solution. The diluted solution is inoculated into an inorganic salt agar medium containing PCNB as solo sources of carbon and nitrogen, and isolation of the decomposing bacteria is carried out by the conventional method, i.e. plate dilution method.

After cultivation for three weeks, clear zones were recognized in a plate medium. Out of the clear zones, one considered to have a high decomposing activity (large in clear zone area) is used for fishing ten strains therefrom. The fished ten strains are further cultured in an inorganic agar medium, and then each inoculated in an inorganic salt medium containing 5 mg/liter of PCNB to examine the decomposing activity of the strains. As a result, six out of ten strains were recognized to have a high decomposing activity.

Figure 6:
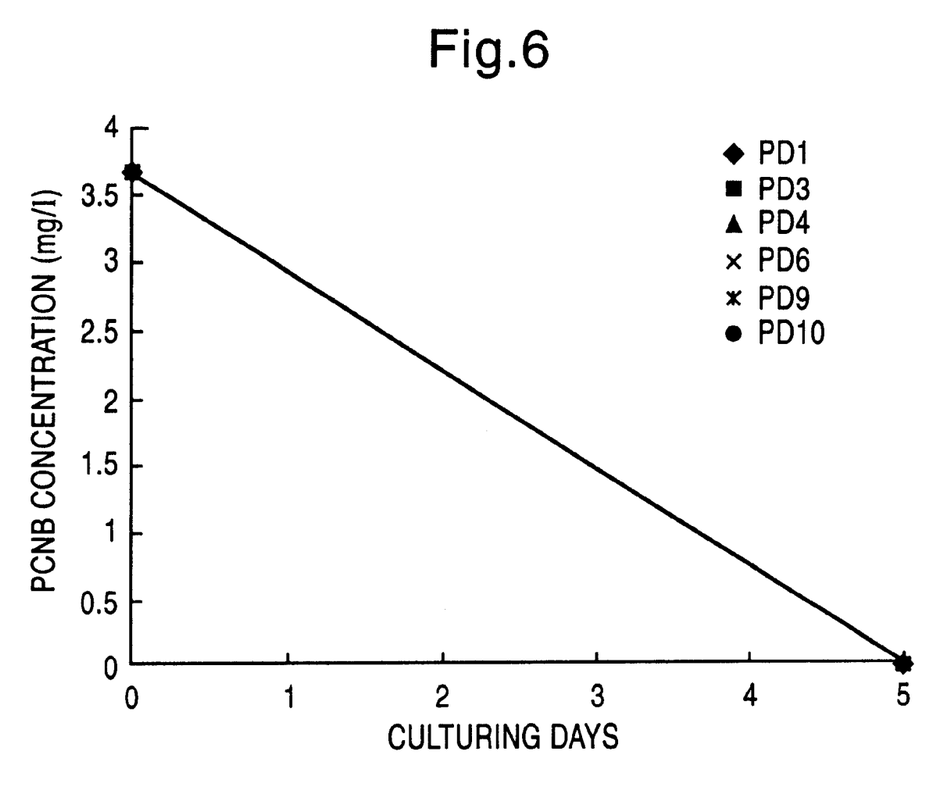
FIG. 6 shows a graph showing the states of decomposition of PCNB by six strains having a high PCNB-decomposing activity, in relation to concentrations of PCNB.
Figure 7:
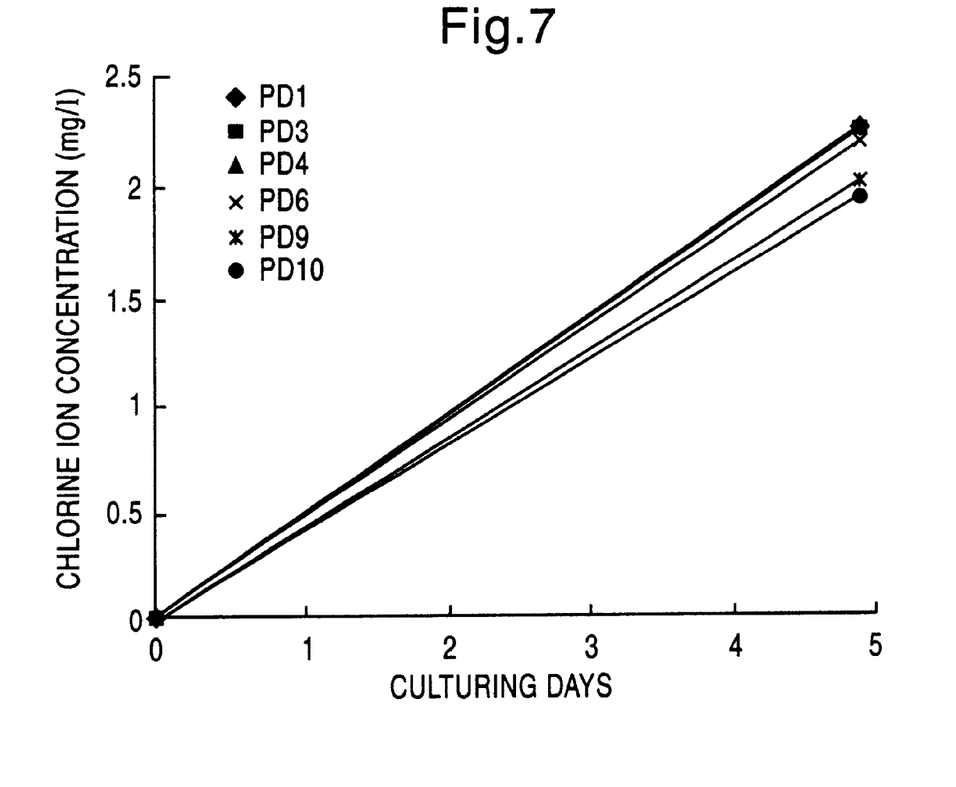
FIG. 7 shows a graph showing the states of decomposition of PCNB by the six strains having a high PCNB-decomposing activity, in relation to concentrations of chlorine ions ($Cl^-$)

The six strains having a high decomposing activity were cultured in inorganic salt agar media, and then a loopful—using an inoculating needle—of each strain was inoculated to 30 ml of an inorganic salt solution containing 3.66 mg/liter of PCNB to examine the decomposing activities. The results are shown in FIGS. 6 and 7. It was recognized that the six strains having a high decomposing activity (PD1, PD3, PD4, PD6, PD9, PD10) each completely decomposed PCNB in five days. Further, FIG. 7 shows results of measurement of chlorine ions ($Cl^-$) as a by-product of decomposition of PCNB, whereby it was confirmed that the six strains each increased the concentration of $Cl^-$ to approximately 2 mg/liter in five days. This value is substantially equal to 2.20 mg/liter i.e. a theoretical $Cl^-$ concentration value which is to be measured when 3.66 mg/liter of PCNB is completely decomposed, and shows that the six strains enriched and isolated by the methods according to the present invention are capable of removing all chlorine atoms in each PCNB molecule (see FIG. 1) therefrom.

Figure 8:
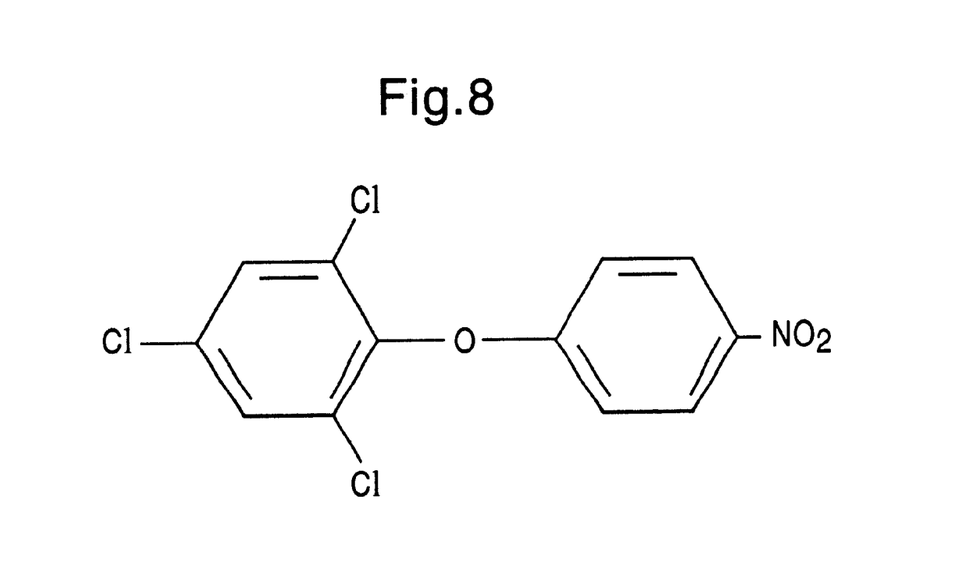
FIG. 8 shows a structural formula of CNP.
Figure 9:
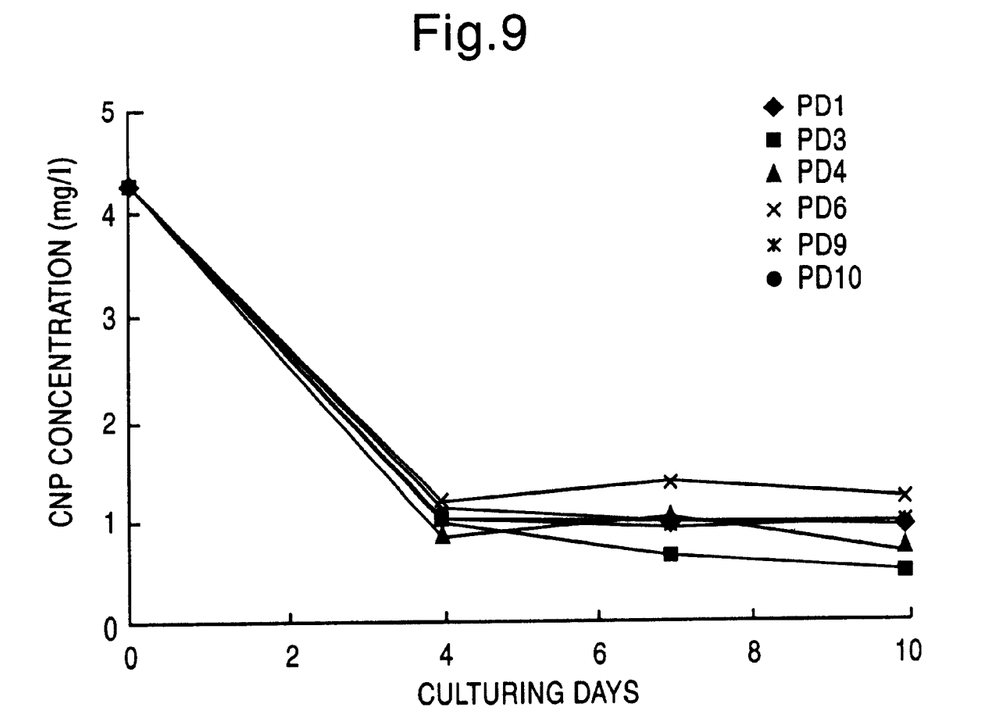
FIG. 9 shows a graph showing the states of decomposition of CNP by the six strains having a high PCNB-decomposing activity, in relation to concentrations of CNP.
Figure 10:
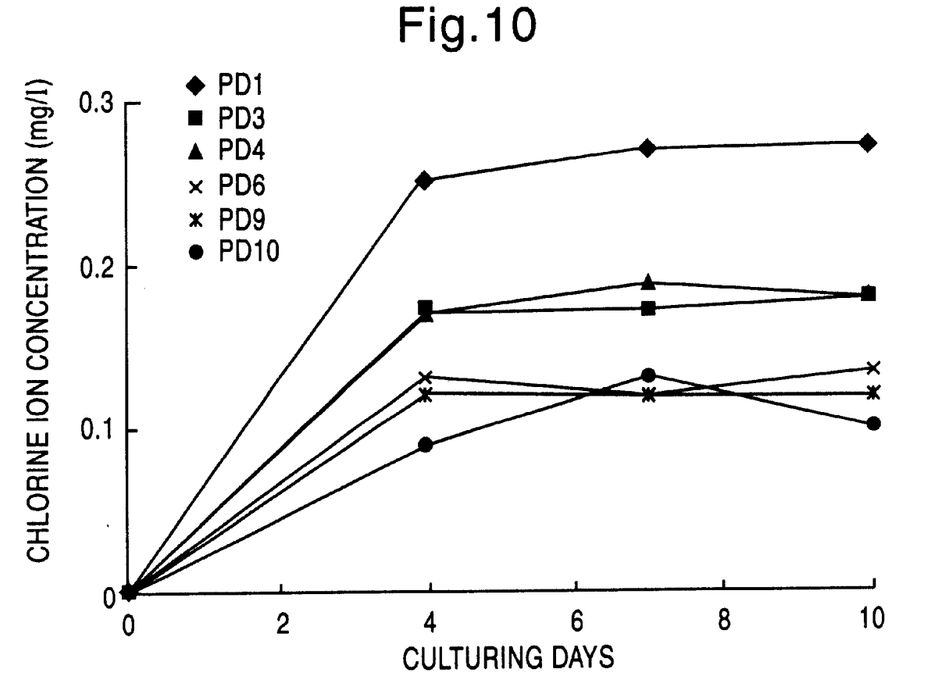
FIG. 10 shows a graph showing the states of decomposition of CNP by the six strains having a high PCNB-decomposing activity, in relation to concentrations of chlorine ions ($Cl^-$)

The six strains having a high PCNB-decomposing activity are used to evaluate their capability of decomposing CNP which is mentioned as one of organochlorine agricultural chemicals difficult to decompose (the structural formula of CNP is shown in FIG. 8). FIGS. 9 and 10 show results of experiments carried out by inoculating a loopful—by using an inoculating needle—of each of the six strains to 30 ml of an inorganic salt solution containing 4.26 mg/liter of CNP for measurement of the PCN-decomposing activity. As shown in the graph of FIG. 9, in all of the six strains having a high PCNB-decomposing activity, the CNP concentration of the inorganic salt solution was decreased from 4.26 mg/liter to approximately 1 mg/liter in four days, whereby it could be confirmed that CNP was being decomposed. However, the decomposition does not proceed further even after the lapse of four days. Further, from results of measurement of concentration of chlorine ions (Cl⁻) as a by-product of CNP decomposition shown in the graph of FIG. 10, even decomposing bacteria PD1 presumably having a highest decomposing capability is recognized to have increased the Cl⁻ concentration to only approximately 0.27 mg/liter at the maximum. Considering that a theoretical chlorine ion concentration to be attained when 4.26 mg/liter of CNP is completely decomposed is equal to 1.42 mg/liter, the decomposition of CNP by the six strains can only remove part of three chlorine atoms present in each CNP molecule the structural formula of which is shown in FIG. 8.

Next, the identification of decomposing bacteria carried out by using the six strains having a high PCNB-decomposing activity (PD1, PD3, PD4, PD6, PD9, and PD10) will be described. By using inorganic salt agar media containing PCNB as solo sources of carbon and nitrogen, purification of the six strains is repeatedly carried out according to a conventional method. Out of the purified six strains, three strains having an even higher PCNB-decomposing activity are selected (PD1, PD3 and PD6). As to the selected three strains, observation of forms of bodies of the decomposing bacteria (in respect of Gram staining, shapes, motility, and shapes of colonies), analysis of aliphatic acid of bodies of the bacteria, quinone analysis, and DNA base composition analysis (content of G+C) were carried out for identification of the decomposing bacteria.

Figure 11:
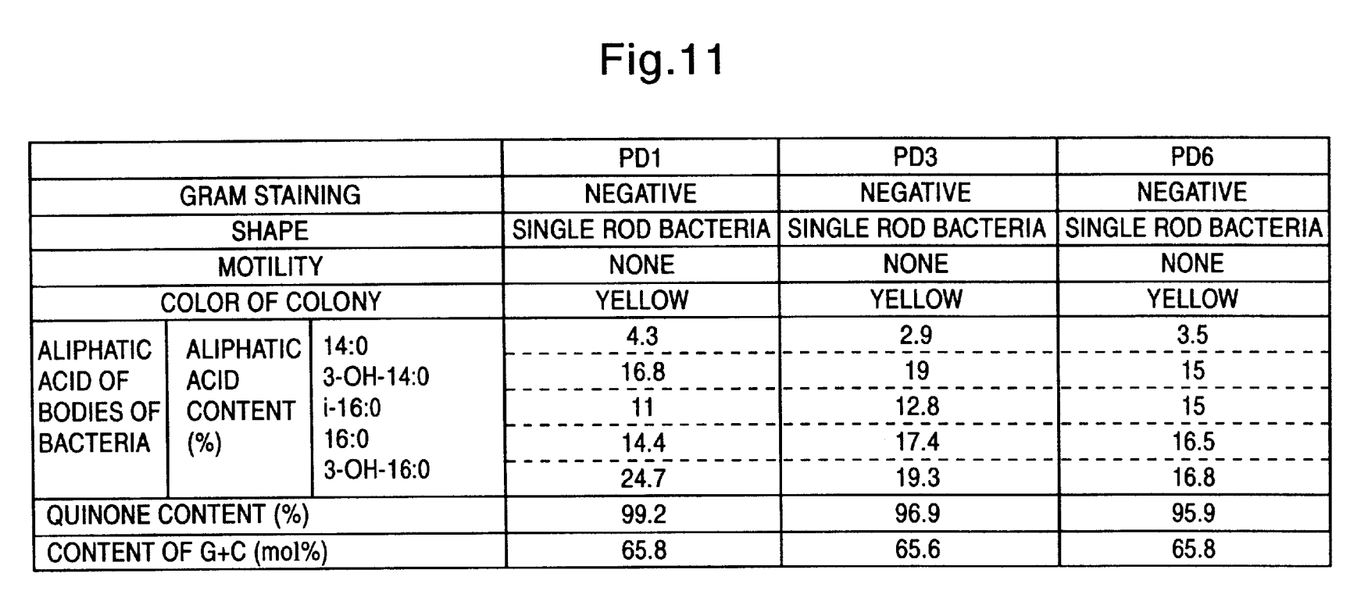
FIG. 11 shows a table of results of identification experiment carried out on three strains having a high PCNB-decomposing activity.

Results of the above experiment for identification of the three strains are shown in Table of FIG. 11. All of the three strains showed that they have a single rod shape, no motility, and negativity of Gram staining. Further, all the three strains can be cultured on bouillon agar plate and form yellow colonies. Then, from the results of the above observation of forms as well as analysis of aliphatic acid of bodies of the bacteria, quinone analysis, and DNA base composition analysis, these three strains were identified to be bacteria having a scientific name of *Burkholderia cepacia* (*Burkholderia cepacia* KTYY97, received on May 18, 1998 by National Institute of Bioscience and Human-Technology, Postal code: 305-0046, No. 1-1-3, Higashi, Tsukuba City, Ibaraki Prefecture, Japan, Receipt No. FERM BP-6721) [identification is carried out based on the following documents: "International journal of Systematic Bacteriology", Vol. 47, No. 4, 1188–1200, (1997), the same journal, Vol. 45, No. 2, 274–289, (1995), "Handbook of New Bacterial Systematics", 196–231, Academic Press, (1993), "Bacterial Identification Method accompanying New Systematics" compiled by Education Committee of Japanese Society for Bacteriology, Saikon Shuppan, 56–64 (1987).] *Burkholderia cepacia* is aerobic bacteria which have a high capability of decomposing an organochlorine agricultural chemical PCNB as descried above.

INDUSTRIAL APPLICABILITY

As described heretofore, the decomposing bacteria *Burkholderia cepacia* of the present invention are capable of decomposing an organochlorine agricultural chemical PCNB, and further one of organochlorine agricultural chemicals difficult to decompose, CNP. This decomposing bacteria are aerobic bacteria, which can be easily applied to dispose of agricultural chemicals remaining in soil, and contributes to a technique of preventing contamination of river water and groundwater by agricultural chemicals.

What is claimed is:

1. A biologically pore culture of aerobic bacteria *Burkholderia cepacia* KTYY97 which aerobically decompose an organochlorine agricultural chemical pentachloronitrobenzene (PCNB).

2. A microorganism according to claim 1, wherein when about 30 ml of an inorganic salt solution containing about 3.66 mg/liter PCNB is inoculated with said microorganism, the PCNB is substantially decomposed within about five days.

3. A microorganism according to claim 2, wherein the concentration of Cl– in said solution increases to about 2 mg/liter within about five days.

4. A microorganism according to claim 1, further capable of reducing the chlornitrofen (CNP) concentration of about 30 ml solution of inorganic salt from about 4.26 mg/liter to about 1 mg/liter within about four days.

5. A method of enriching PCNB-decomposing aerobic bacteria *Burkholderia cepacia* KTYY97 in a Fragmented porous material comprising mixing a soil containing said aerobic bacteria and PCNB with a fragmented porous material having a number of micropores and at the same time a greater adsorptivity for adsorbing PCNB than said soil to form an enrichment soil layer, and circulating through said enrichment soil layer an inorganic salt medium containing a carbon and nitrogen source, said carbon and nitrogen source being formed only of PCNB, thereby enriching said fragmented porous material with said aerobic bacteria *Burkholderia cepacia*.

6. A method of preparing decomposing bacteria *Burkholderia cepacia* KTYY97 for isolation thereof comprising mixing said fragmented porous material enriched with said aerobic bacteria *Burkholderia cepacia* prepared by the method of claim 5 into a new fragmented porous material to form an enrichment layer consisting of the fragmented porous material only, and circulating through said enrichment layer an inorganic salt medium containing a carbon and nitrogen source, said carbon and nitrogen source being formed only of PCNB, thereby effecting increasing said aerobic bacteria *Burkholderia cepacia* in said new fragmented porous material.

7. An organochlorine agricultural chemical-decomposing holdback carrier comprising a porous material holding aerobic bacteria *Burkholderia cepacia* KTYY97 obtained by the method of claim 6.

8. An organochlorine agricultural chemical-decomposing holdback carrier comprising a porous material holding PCNB-decomposing aerobic bacteria *Burkholderia cepacia* KTYY97.

9. A carrier according to claim 8, wherein said porous material holding aerobic bacteria is obtained by:
   mixing a soil containing aerobic bacteria *Burkholderia cepacia* KTTY97 and PCNB with a fragmented porous material having a number of micropores and at the same time a greater adsorptivity for adsorbing PCNB than said soil to form an enrichment soil layer; and
   circulating an inorganic salt medium comprising a carbon and nitrogen source through said enrichment soil layer, said carbon and nitrogen source being formed only of PCNB to form said porous material.

10. A carrier according to claim 8, wherein said porous material holding aerobic bacteria is obtained by:

mixing a first porous material enriched with said aerobic PCNB-decomposing bacteria with a second porous material to form an enrichment layer; and, circulating an inorganic salt medium containing a carbon and nitrogen source through said enrichment soil layer, said carbon and nitrogen source being formed only of PCNB to form a further enriched porous material.

11. A method of enriching PCNB-decomposing aerobic bacteria *Burkholderia cepacia* KTYY97 in a porous material, comprising:

mixing a soil comprising said anaerobic bacteria and PCNB with a first porous material to form an enrichment layer, wherein the adsorptivity for adsorbing PCNB of said porous material is greater than the adsorptivity for adsorbing PCNB of said soil; and circulating an inorganic salt medium comprising a carbon and nitrogen source through said enrichment layer, said carbon and nitrogen source being formed only of PCNB to produce a first enriched porous material.

12. A method according to claim 11, wherein said porous material is up to about ten mm is size.

13. A method according to claim 11, wherein said porous material is a charcoal material.

14. A method according to claim 11, further comprising:

mixing the enriched first porous material with a second porous material to form an enrichment layer; and circulating an inorganic salt medium containing a carbon and nitrogen source through said enrichment layer; said carbon and nitrogen source being formed only by PCNB to produce a further enriched porous material.

15. A method of isolating decomposing PCBNB-decomposing bacteria *Burkholderia cepacia* KTYY97 by means of decomposing bacteria *Burkholderia cepacia* KTYY97 by means of the enriching method as set forth in claim 14, further comprising isolating said bacteria from the enriched first and second porous materials.

16. A method according to claim 14, wherein said first and second porous materials are charcoal materials.

* * * * *

UNITED STATES PATENT AND TRADEMARK OFFICE
CERTIFICATE OF CORRECTION

PATENT NO.    : 6,498,028 B1
DATED         : December 24, 2002
INVENTOR(S)   : Takagi et al.

It is certified that error appears in the above-identified patent and that said Letters Patent is hereby corrected as shown below:

Column 8,
Line 7, replace "pore" with -- pure --.
Line 23, replace "Fragmented" with -- fragmented --.

Column 9,
Line 20, replace "is" with -- in --.

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,498,028 B1
DATED : December 24, 2002
INVENTOR(S) : Takagi et al.

It is certified that error appears in the above-identified patent and that said Letters Patent is hereby corrected as shown below:

Column 8,
Line 44, delete "effecting".

Column 10,
Line 6, add ",";
Line 9, replace "by" with -- of --.

Signed and Sealed this

Twelfth Day of August, 2003

JAMES E. ROGAN
*Director of the United States Patent and Trademark Office*